United States Patent
Norman

(10) Patent No.: US 10,857,079 B2
(45) Date of Patent: Dec. 8, 2020

(54) MASCARA FORMULATION

(71) Applicant: Mary Kay Inc., Addison, TX (US)

(72) Inventor: Greg Norman, Addison, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 16/298,771

(22) Filed: Mar. 11, 2019

(65) Prior Publication Data

US 2019/0336412 A1 Nov. 7, 2019

Related U.S. Application Data

(63) Continuation of application No. 14/662,994, filed on Mar. 19, 2015, now abandoned.

(60) Provisional application No. 61/955,651, filed on Mar. 19, 2014.

(51) Int. Cl.

| A61K 8/06 | (2006.01) |
| A61K 8/92 | (2006.01) |
| A61K 8/86 | (2006.01) |
| A61K 8/37 | (2006.01) |
| A61K 8/36 | (2006.01) |
| A61Q 1/10 | (2006.01) |
| A61K 8/31 | (2006.01) |

(52) U.S. Cl.
CPC ............... *A61K 8/062* (2013.01); *A61K 8/31* (2013.01); *A61K 8/361* (2013.01); *A61K 8/37* (2013.01); *A61K 8/86* (2013.01); *A61K 8/922* (2013.01); *A61K 8/927* (2013.01); *A61Q 1/10* (2013.01)

(58) Field of Classification Search
None
See application file for complete search history.

(56) References Cited

U.S. PATENT DOCUMENTS

| 5,763,497 A | 6/1998 | Ikeda et al. |
| 5,849,278 A * | 12/1998 | Piot .................. A61K 8/044 424/70.7 |
| 7,220,432 B2 | 5/2007 | Dee et al. |
| D616,608 S | 5/2010 | Maddy |
| 2003/0147830 A1 | 8/2003 | Phillips et al. |
| 2006/0159642 A1 | 7/2006 | Hanna et al. |
| 2007/0036739 A1 | 2/2007 | Feng |
| 2007/0154439 A1 | 7/2007 | Dorf |
| 2007/0246058 A1 | 10/2007 | Bodelin |
| 2009/0035242 A1 | 2/2009 | Maes et al. |
| 2009/0142289 A1 | 6/2009 | Arditty et al. |
| 2011/0097289 A1 | 4/2011 | Viala et al. |
| 2011/0150807 A1 | 6/2011 | Bui et al. |
| 2012/0308504 A1 | 12/2012 | Andreo et al. |
| 2014/0105942 A1* | 4/2014 | Pistorio ................ C09D 191/06 424/401 |

FOREIGN PATENT DOCUMENTS

| CN | 102524514 | 4/2013 |
| JP | 2009-235029 | 10/2009 |
| WO | WO 2013/083532 | 6/2013 |
| WO | WO 2013/190080 | 12/2013 |

OTHER PUBLICATIONS

Anon "Antimicrobial mixtures," ip.com, 2010.*
International Search Report and Written Opinion in PCT/US2015/021503, dated May 29, 2015.
Schaefer, "Synthetic Mica Pigments for Color Cosmetics," Cosmetics & Toiletries, Jun. 21, 2011; http://www.cosmeticsandtoiletries.com/formulating/function/pigment/124181714.html.
Sedlewicz "Current Trends in Cosmetic Preservation," Sep. 23, 2011; http://www.midwestscc.org/blog2/wp-content/uploads/presentations/Jan2012CurrentTrendsInCosmeticPreservation.pdf ; google date for Sedlewicz showing online availability as of Jan. 12, 2012, printed 2016.

* cited by examiner

*Primary Examiner* — Ileana Popa
*Assistant Examiner* — Alissa Prosser
(74) *Attorney, Agent, or Firm* — Norton Rose Fulbright US LLP

(57) ABSTRACT

Disclosed is an oil-in-water anionic emulsion for eyelashes, and methods for its use, comprising a continuous phase comprising 35 to 55% by weight of water based on the total weight of the emulsion, a discontinuous phase comprising 15 to 25% by weight of a combination of waxes, wherein the combination of waxes comprises paraffin wax, carnauba wax, beeswax, and candelilla wax based on the total weight of the emulsion, and 5 to 15% by weight of the emulsion of an anionic surfactant system comprising stearic acid, palmitic acid, myristic acid, polyethylene glycol-40 (PEG-40) stearate, and stearyl stearate, wherein the oil-in-water anionic emulsion is capable of thickening the appearance of eyelashes.

19 Claims, 1 Drawing Sheet

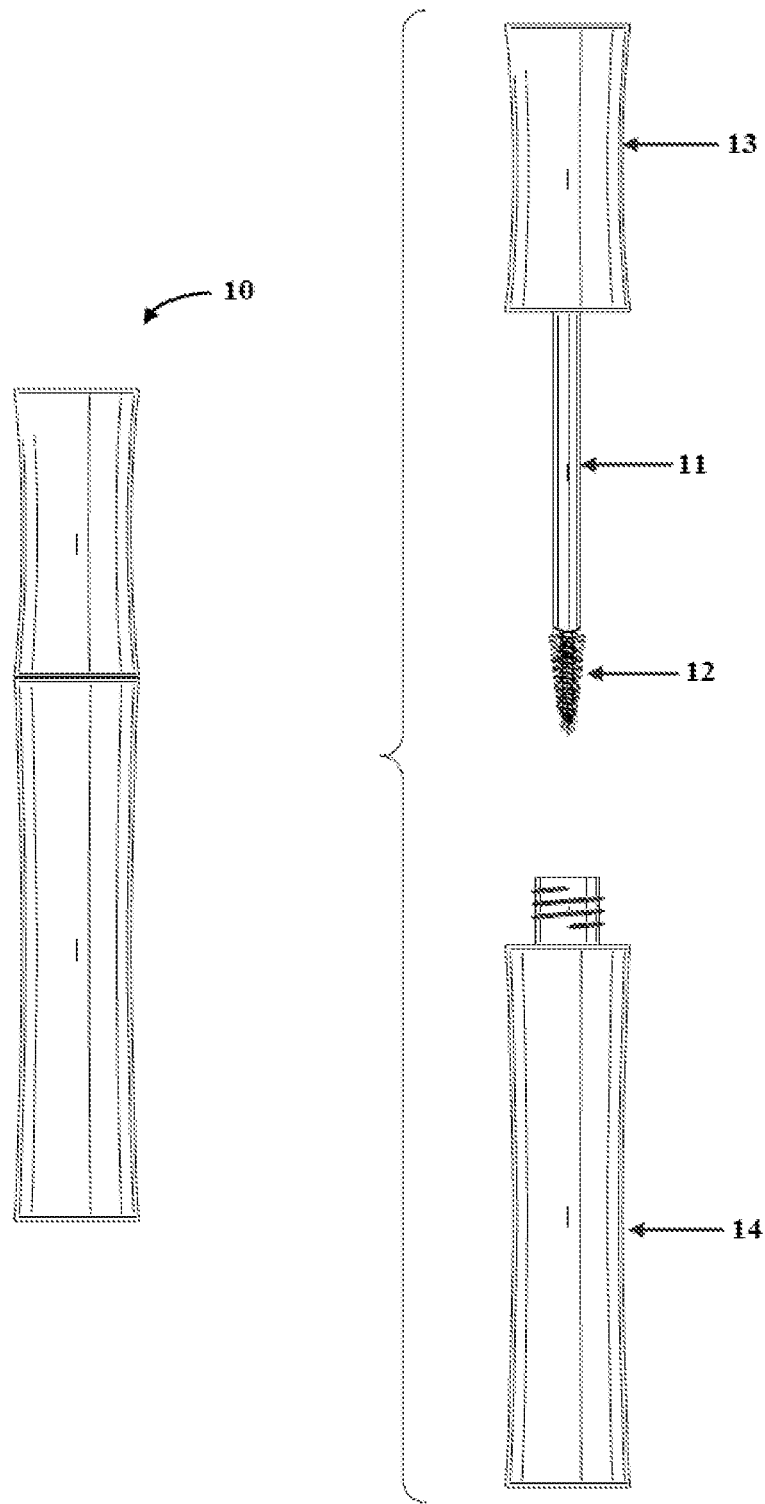

MASCARA FORMULATION

CROSS REFERENCE TO RELATED APPLICATIONS

This application is a continuation of U.S. patent application Ser. No. 14/662,994, filed Mar. 19, 2015, which claims the benefit of U.S. Provisional Application 61/955,651 filed on Mar. 19, 2014. The contents of the referenced applications are incorporated into the present application by reference.

BACKGROUND OF THE INVENTION

A. Field of the Invention

The present invention relates generally to a mascara formulation that can be used to increase the volume or thicken the appearance of eyelashes.

B. Description of Related Art

There are a variety of commercially available mascaras that claim to thicken or enhance the volume of eyelashes. A majority of these formulations tend to have a greasy or "heavy" tactile feel due to their reliance on large amounts of occlusive ingredients such as waxes (e.g., lanolin) to create the thickening effect. Further, such formulations oftentimes tend to coalesce or clump together, which results in eyelashes that have an uneven and unsightly visual appearance thereby defeating the purpose of using the mascara product.

SUMMARY OF THE INVENTION

A solution has been discovered to the aforementioned problems associated with mascaras that are designed to thicken eyelashes. The solution is premised on the creation of an oil-in-water anionic emulsion system in combination with a wax blend. Without wishing to be bound by theory, it is believed that the anionic emulsion system allows for increased amounts of water into the formula, thus creating a formula having a lighter or less greasy feel that is also less likely to clump or coalesce together. The wax blend can then be used in sufficient amounts to impart the desired thickening properties to the formulation. This combination results in an easy to spread/apply mascara formulation that has the ability to thicken eyelash hairs or fibers while also avoiding the so-called clumping characteristics seen with the currently available mascara formulations.

In one aspect of the present invention there is disclosed an oil-in-water anionic emulsion for eyelashes (e.g., a mascara). The emulsion can include: (a) a continuous phase comprising 35 to 55% by weight of water based on the total weight of the emulsion; (b) a discontinuous phase comprising 15 to 25% by weight of a combination of waxes, wherein the combination of waxes comprises paraffin wax, carnauba wax, beeswax, and candelilla wax based on the total weight of the emulsion; and (c) 5 to 15% by weight of the emulsion of an anionic surfactant system comprising stearic acid, palmitic acid, myristic acid, polyethylene glycol-40 (PEG-40) stearate, and stearyl stearate, wherein the oil-in-water anionic emulsion is capable of thickening the appearance of eyelashes. The oil-in-water anionic emulsion can be capable of thickening the appearance of a hair fiber such as an eyelash. Thickening the appearance also refers to increasing the total volume of the eyelash, which can be subjectively determined by visual inspection (e.g., comparing an eyelash having the composition with the same eyelash in which the composition is removed) or objectively measured with standard mathematical equations that calculate the volume of an elongated cylinder. The oil-in-water anionic emulsion can include 14 to 17% by weight of paraffin wax, 2 to 5% by weight of carnuba wax, 2 to 5% by weight of beeswax, and 0.5 to 2% by weight of candelilla wax. The oil-in-water anionic emulsion can include 2 to 5% by weight of stearic acid, 2 to 5% by weight of palmitic acid, 0.1 to 1% by weight of myristic acid, 0.5 to 2% by weight of PEG-40 stearate, and 0.5 to 2% by weight of stearyl stearate. The oil-in-water anionic emulsion can include VP/Eicosene copolymer, trimethylpentanediol/adipic acid/glycerin cross polymer, hydroxyethylcellulose, and bis-diglyceryl polyacyladipate-2. The oil-in-water anionic emulsion can include 0.1 to 1% by weight of VP/Eicosene copolymer, 0.5 to 2% by weight of trimethylpentanediol/adipic acid/glycerin cross polymer, 0.1 to 1% by weight of hydroxyethylcellulose, and 2 to 5% by weight of bis-diglyceryl polyacyladipate-2. The oil-in-water anionic emulsion can include iron oxide, triethanolamine, silica, benzyl alcohol, nylon-12, caprylyl glycol, and dimethicone. The oil-in-water anionic emulsion can include 5 to 15% by weight of iron oxide, 1 to 5% by weight of triethanolamine, 0.1 to 2% by weight of silica, 0.1 to 2% by weight of benzyl alcohol, 0.1 to 1% by weight of nylon-12, 0.1 to 1% by weight of caprylyl glycol, and 0.1 to 1% by weight of dimethicone. The oil-in-water anionic emulsion can include any one of, any combination of, or all of chlorphenesin, panthenol, sorbitan stearate, synthetic fluorphlogopite, tocopheryl acetate, disodium EDTA, tocopheryl acetate, and cyclohexasiloxane. In particular aspects, the emulsion is adapted to increase the length or bulk or volume of a person's eyelash hair or fiber. The composition can also include pigments, dyes, colorants, etc., to achieve a desired color of the composition. The composition can be water resistant. The emulsion can be adapted to form a smooth surface when applied to a keratinous fiber. In particular aspects, the emulsion can be included on/loaded onto an applicator tip of a mascara wand and then applied to eyelashes.

Also disclosed is a method of applying any one of oil-in-water anionic emulsions of the present invention to eyelashes. The method can include using a mascara wand to apply the emulsion to eyelash hairs or fibers. A mascara wand can include an elongated portion having an applicator tip. The applicator tip can be designed to hold the emulsion of the present invention and to transfer the emulsion from the tip to eyelashes. The thickness or volume of the eyelash becomes greater after application of the emulsion to the eyelash hair or fiber.

Water-resistance means that the composition has the ability to remain on the hair shaft despite being subjected to removal by water such as rinsing of a face, rain, or tears. Smudge-resistance means that the composition has the ability to remain on the hair shaft despite being subjected to frictional forces such as normal rubbing of the eye area with one's hand. It was discovered that the combination of the wax blend and anionic emulsion system creates such a mascara.

The formulations can increase the volume of a hair shaft by 2 times, 3 times, 4 times, or 5 times the original volume of the hair shaft, with volume being measured by standard mathematical equations for the shape of the shaft (e.g., cylinder, irregular prism, rectangle, etc., as the shape of a given shaft may vary, so may the appropriate equation). The length of the hair shaft can also be lengthened, which can be measured by determining the length of a hair shaft prior to and post application of a given mascara.

In some embodiments, the mascara composition can comprise a suitable pigment. Such pigments can be inorganic pigments, organic lake pigments, pearlesent pigments, and mixtures thereof. In some embodiments, the inorganic pigments can be selected from the group consisting of rutile and anatase titanium dioxide, black, yellow, red and brown iron oxides, manganese violet, ultramarine blue, chromium oxide, chromium hydrate, or ferric blue; or any combination thereof.

Also contemplated are kits that include any one of the compositions disclosed throughout the specification and claims. In certain embodiments, the composition is comprised in a container. The container can be a bottle, dispenser, or package. In more particular embodiments, the container can include a base and a cap, with the cap further including an applicator such as a wand with a brush, comb, or wire structure at the distal end of the wand. The container can include indicia on its surface. The indicia can be a word, an abbreviation, a picture, or a symbol.

The compositions and methods for their use can "comprise," "consist essentially of," or "consist of" any of the ingredients disclosed throughout the specification. For purposes of consisting essentially of means that inclusion of additional ingredients in the compositions do not materially affect the beneficial properties of the compositions such as making lashes appear longer and/or thicker or making the mascara composition more smudge resistant and/or water-resistant.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," "treating," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions of the present invention is their ability to increase the volume of an eyelash hair or fiber.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

FIG. 1: Mascara container that can be used to apply the composition of the present invention to eyelashes.

DESCRIPTION OF ILLUSTRATIVE EMBODIMENTS

The inventor discovered a mascara that can be used to make the eyelashes appear longer and thicker. The discovery is based on the combination of an anionic surfactant system and a wax blend. In particular, the anionic surfactant system can include stearic acid, palmitic acid, myristic acid, polyethylene glycol-40 (PEG-40) stearate, and stearyl stearate. The amount of this surfactant system can range from 5 to 15% by weight of the composition. With respect to the wax blend, it can include a combination of paraffin wax, carnauba wax, beeswax, and candelilla wax. The amount of the waxes in the composition can range from 15 to 25% by weight of the composition. As shown in the below example composition, additional ingredients can also be added to the formulation to provide various tactile properties, consistency, viscosity, etc. Notably, all of the ingredients in the formulation are commercially available. Examples of suppliers are provided in the International Cosmetic Ingredient Dictionary and Handbook, 12$^{th}$ Edition (2008), the sections of which are incorporated into the present application by reference.

Oil-in-water emulsions such as the present invention include a continuous aqueous phase and a discontinuous oil phase. The aqueous phase in the context of the present invention can include water in an amount of 35 to 55% by weight of the total emulsion. Additional hydrophilic ingredients are included in the aqueous phase. The discontinuous oil phase can include the wax blend in an amount of 15 to 25% by weight of the total emulsion. Additional hydrophobic ingredients are included in the discontinuous oil phase. The anionic surfactant system used to create the emulsion can be used in an amount of 5 to 15% by weight of the total emulsion. Additional ingredients and excipients can be included in the emulsion to achieve desired characteristics (e.g., viscosity or tactile properties) and stability (e.g., chelating agents and preservatives).

FIG. 1 illustrates a mascara container 10 that can be used to apply the emulsions of the present invention to eyelashes. The container 10 can include an elongated portion or wand 11 and an applicator tip 12 coupled to the end of the wand 11 portion. The wand portion 11 can be coupled to a cap 13 of the container 10. The emulsions of the present invention can be stored in the body or base 14 portion of the container 10.

Table 1 describes a non-limiting mascara formulation of the present invention. The Table 1 formulation is an oil-in-water anionic emulsion that can increase the thickness of eyelashes by application of the emulsion to eyelash hairs.

TABLE 1

| Ingredient | % Concentration (by weight) |
| --- | --- |
| Water | 45 |
| Paraffin | 16 |
| Iron oxides | 10 |
| Stearic acid | 4 |
| Palmitic acid | 3 |
| Carnauba Wax | 3 |
| bis-diglyceryl polyacyladipate-2 | 3 |
| Beeswax | 3 |
| Triethanolamine | 2 |
| Stearyl stearate | 1 |
| Trimethylpentanediol/adipic acid/glycerin crosspolymer | 1 |
| Silica | 1 |
| PEG-40 stearate | 1 |
| Candelilla wax | 1 |
| Benzyl alcohol | 1 |
| Nylon-12 | 0.7 |
| Myristic acid | 0.5 |
| VP/Eicosene copolymer | 0.5 |
| Caprylyl glycol | 0.5 |
| Dimethicone | 0.5 |
| Hydroxyethylcellulose | 0.4 |
| Excipients | q.s. |

The emulsion was prepared by standard techniques known in the cosmetic industry. In particular, the water phase ingredients and oil phase ingredients and surfactants were added to a mixing tank and mixed under heat until a homogenous composition was obtained. The composition was then cooled to room temperature (20-25° C.). Excipients were added to the formulation to achieve stability (e.g., chelating agents and preservatives). The excipients included chlorphenesin, panthenol, sorbitan stearate, synthetic fluorophlogopite, tocopheryl acetate, disodium EDTA, and cyclohexasiloxane. Notably, however, no excipients need to be added and the formulation can be q.s.'d with water.

The above example formulation is included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Also, all of the ingredients, compositions, or methods disclosed and claimed in this specification can be made and executed without undue experimentation in light of the present disclosure. While the ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method of thickening the appearance of eyelashes and increasing the volume of eyelashes, the method consisting of directly applying an oil-in-water anionic emulsion to eyelashes, wherein:
   direct application of the oil-in-water anionic emulsion to the eyelashes thickens the appearance of the eyelashes and increases the volume of the eyelashes; and
   the oil-in-water anionic emulsion comprises:
      (a) a continuous phase comprising 35 to 55% by weight of water based on the total weight of the emulsion;
      (b) a discontinuous phase comprising 15 to 25% by weight of a combination of waxes, wherein the combination of waxes comprises paraffin wax, carnauba wax, beeswax, and candelilla wax based on the total weight of the emulsion;
      (c) 5 to 15% by weight of the emulsion of an anionic surfactant system comprising stearic acid, palmitic acid, myristic acid, polyethylene glycol-40 (PEG-40) stearate, and stearyl stearate; and
      (d) VP/Eicosene copolymer, trimethylpentanediol/adipic acid/glycerin cross polymer, hydroxyethylcellulose, and bis-diglyceryl polyacyladipate-2.

2. The method of claim 1, wherein the oil-in-water anionic emulsion is applied to the eyelashes with a mascara wand.

3. The method of claim 1, wherein the oil-in-water anionic emulsion comprises:
   15 to 17 wt. % paraffin wax;
   5 to 15 wt. % iron oxides;
   2 to 5 wt. % stearic acid;
   2 to 5 wt. % palmitic acid;
   2 to 5 wt. % carnauba wax;
   3 wt. % bis-diglyceryl polyacyladipate-2;
   2 to 5 wt. % beeswax;
   1 to 5 wt. % triethanolamine;
   0.5 to 2 wt. % stearyl stearate;
   0.5 to 2 wt. % trimethylpentanediol/adipic acid/glycerin crosspolymer;
   0.1 to 2 wt. % silica;
   0.5 to 2 wt. % PEG-40 stearate;
   0.5 to 2 wt. % candelilla wax;
   0.1 to 2 wt. % benzyl alcohol;
   0.1 to 1 wt. % nylon-12;
   0.1 to 1 wt. % myristic acid;
   0.1 to 1 wt. % VP/eicosene copolymer;
   0.1 to 1 wt. % caprylyl glycol;
   0.1 to 1 wt. % dimethicone; and
   0.1 to 1 wt. % hydroxyethylcellulose.

4. The method of claim 1, wherein the oil-in-water anionic emulsion comprises 15 to 17 wt. % paraffin wax, 2 to 5 wt. % carnauba wax, 2 to 5 wt. % beeswax, and 0.5 to 2 wt. % candelilla wax.

5. The method of claim 1, wherein the oil-in-water anionic emulsion comprises 2 to 5 wt. % stearic acid, 2 to 5 wt. % palmitic acid, 0.1 to 1 wt. % myristic acid, 0.5 to 2 wt. % PEG-40 stearate, and 0.5 to 2 wt. % stearyl stearate.

6. The method of claim 1, wherein the oil-in-water anionic emulsion comprises 0.1 to 1 wt. % VP/Eicosene copolymer, 0.5 to 2 wt. % trimethylpentanediol/adipic acid/glycerin cross polymer, 0.1 to 1 wt. % hydroxyethylcellulose, and 2 to 5 wt. % bis-diglyceryl polyacyladipate-2.

7. The method of claim 1, wherein the oil-in-water anionic emulsion further comprises iron oxide, triethanolamine, silica, benzyl alcohol, nylon-12, caprylyl glycol, and dimethicone.

8. A method of thickening the appearance of eyelashes and increasing the volume of eyelashes, the method consisting of directly applying an oil-in-water anionic emulsion to eyelashes, wherein direct application of the oil-in-water anionic emulsion to the eyelashes thickens the appearance of the eyelashes and increases the volume of the eyelashes, and wherein the oil-in-water anionic emulsion comprises:
  (a) a continuous phase comprising 35 to 55% by weight of water based on the total weight of the emulsion;
  (b) a discontinuous phase comprising 15 to 25% by weight of a combination of waxes, wherein the combination of waxes comprises paraffin wax, carnauba wax, beeswax, and candelilla wax based on the total weight of the emulsion;
  (c) 5 to 15% by weight of the emulsion of an anionic surfactant system comprising stearic acid, palmitic acid, myristic acid, polyethylene glycol-40 (PEG-40) stearate, and stearyl stearate; and
  (d) 5 to 15 wt. % iron oxide, 1 to 5 wt. % triethanolamine, 0.1 to 2 wt. % silica, 0.1 to 2 wt. % benzyl alcohol, 0.1 to 1 wt. % nylon-12, 0.1 to 1 wt. % caprylyl glycol, and 0.1 to 1 wt. % dimethicone.

9. The method of claim 8, wherein the oil-in-water anionic emulsion is applied to the eyelashes with a mascara wand.

10. The method of claim 8, wherein the oil-in-water anionic emulsion comprises 15 to 17 wt. % paraffin wax, 2 to 5 wt. % carnauba wax, 2 to 5 wt. % beeswax, and 0.5 to 2 wt. % candelilla wax.

11. The method of claim 8, wherein the oil-in-water anionic emulsion comprises 2 to 5 wt. % stearic acid, 2 to 5 wt. % palmitic acid, 0.1 to 1 wt. % myristic acid, 0.5 to 2 wt. % PEG-40 stearate, and 0.5 to 2 wt. % stearyl stearate.

12. The method of claim 8, wherein the oil-in-water anionic emulsion further comprises VP/Eicosene copolymer, trimethylpentanediol/adipic acid/glycerin cross polymer, hydroxyethylcellulose, and bis-diglyceryl polyacyladipate-2.

13. The method of claim 8, wherein the oil-in water anionic emulsion further comprises chlorphenesin, panthenol, sorbitan stearate, synthetic fluorphlogopite, tocopheryl acetate, disodium EDTA, and cyclohexasiloxane.

14. A method of thickening the appearance of eyelashes and increasing the volume of eyelashes, the method consisting of directly applying an oil-in-water anionic emulsion to eyelashes, wherein direct application of the oil-in-water anionic emulsion to the eyelashes thickens the appearance of the eyelashes and increases the volume of the eyelashes, and wherein the oil-in-water anionic emulsion comprises:
  (a) a continuous phase comprising 35 to 55% by weight of water based on the total weight of the emulsion;
  (b) a discontinuous phase comprising 15 to 25% by weight of a combination of waxes, wherein the combination of waxes comprises paraffin wax, carnauba wax, beeswax, and candelilla wax based on the total weight of the emulsion;
  (c) 5 to 15% by weight of the emulsion of an anionic surfactant system comprising stearic acid, palmitic acid, myristic acid, polyethylene glycol-40 (PEG-40) stearate, and stearyl stearate; and
  (d) chlorphenesin, panthenol, sorbitan stearate, synthetic fluorphlogopite, tocopheryl acetate, disodium EDTA, and cyclohexasiloxane.

15. The method of claim 14, wherein the oil-in-water anionic emulsion is applied to the eyelashes with a mascara wand.

16. The method of claim 14, wherein the oil-in-water anionic emulsion comprises 15 to 17 wt. % paraffin wax, 2 to 5 wt. % carnauba wax, 2 to 5 wt. % beeswax, and 0.5 to 2 wt. % candelilla wax.

17. The method of claim 14, wherein the oil-in-water anionic emulsion comprises 2 to 5 wt. % stearic acid, 2 to 5 wt. % palmitic acid, 0.1 to 1 wt. % myristic acid, 0.5 to 2 wt. % PEG-40 stearate, and 0.5 to 2 wt. % stearyl stearate.

18. The method of claim 14, wherein the oil-in-water anionic emulsion further comprises VP/Eicosene copolymer, trimethylpentanediol/adipic acid/glycerin cross polymer, hydroxyethylcellulose, and bis-diglyceryl polyacyladipate-2.

19. The method of claim 14, wherein the oil-in-water anionic emulsion further comprises iron oxide, triethanolamine, silica, benzyl alcohol, nylon-12, caprylyl glycol, and dimethicone.

* * * * *